United States Patent [19]

Oppong

[11] Patent Number: 5,328,926
[45] Date of Patent: Jul. 12, 1994

[54] SYNERGISTIC COMBINATIONS OF IODOPROPARGYL COMPOUNDS WITH 1,2-BENZISOTHIAZOLIN-3-ONE IN CONTROLLING FUNGAL AND BACTERIAL GROWTH IN AQUEOUS FLUIDS

[75] Inventor: David Oppong, Memphis, Tenn.

[73] Assignee: Buckman Laboratories International, Inc., Memphis, Tenn.

[21] Appl. No.: 24,812

[22] Filed: Mar. 1, 1993

Related U.S. Application Data

[63] Continuation of Ser. No. 788,890, Nov. 7, 1991, abandoned.

[51] Int. Cl.$^5$ .................... A01N 43/80; A01N 47/10
[52] U.S. Cl. .................... 514/372; 514/478; 514/479
[58] Field of Search .................... 514/372, 478, 479

[56] References Cited

U.S. PATENT DOCUMENTS

| | | | |
|---|---|---|---|
| 3,517,022 | 6/1970 | Miller et al. | 260/304 |
| 3,879,445 | 4/1975 | Gray et al. | 260/476 R |
| 3,923,870 | 12/1975 | Singer | 260/482 C |
| 3,970,755 | 7/1976 | Gazzard et al. | 424/263 |
| 4,158,655 | 6/1979 | Brady | 260/45.75 B |
| 4,259,350 | 3/1981 | Morisawa et al. | 549/71 |
| 4,592,773 | 6/1986 | Tanaka et al. | 71/88 |
| 4,616,004 | 10/1986 | Edwards | 514/63 |
| 4,719,227 | 1/1988 | Schade et al. | 514/452 |
| 4,830,657 | 5/1989 | Jakubowski et al. | 71/67 |
| 4,945,109 | 7/1990 | Rayudu | 514/478 |
| 5,219,875 | 6/1993 | Sherba et al. | 514/373 |

FOREIGN PATENT DOCUMENTS

| | | |
|---|---|---|
| 0431752A2 | 6/1991 | European Pat. Off. |
| 848130 | 9/1960 | United Kingdom |
| 861379 | 2/1961 | United Kingdom |
| 884541 | 12/1961 | United Kingdom |
| 976028 | 11/1964 | United Kingdom |
| 2208474 | 4/1989 | United Kingdom |
| 2230190 | 10/1990 | United Kingdom |

OTHER PUBLICATIONS

Prog. Industrial Microbiology, 13:121 (1974); "The Deterioration of Metalworking Fluids", Bennett.
Computer Abstract of Japanese Patent No. 6071-009, dated Apr. 22, 1985, Sanyo Chemical Industries, Ltd.
Computer Printout of Japanese Patent No. 2087-230, dated Mar. 28, 1990, Toyo Communication Equip.

*Primary Examiner*—Allen J. Robinson
*Attorney, Agent, or Firm*—Finnegan, Henderson, Farabow, Garrett & Dunner

[57] ABSTRACT

Synergistic combinations of iodopropargyl compounds and 1,2-benzisothiazolin-3-one for use in controlling the growth of at least one microorganism, such as fungi and bacteria in aqueous fluids, such as metalworking fluids.

19 Claims, No Drawings

SYNERGISTIC COMBINATIONS OF IODOPROPARGYL COMPOUNDS WITH 1,2-BENZISOTHIAZOLIN-3-ONE IN CONTROLLING FUNGAL AND BACTERIAL GROWTH IN AQUEOUS FLUIDS

This application is a continuation of application Ser. No. 07/788,890, filed Nov. 7, 1991, now abandoned.

BACKGROUND OF THE INVENTION

1. Field of the Invention

The invention relates to synergistic antimicrobial combinations of iodopropargyl compounds with 1,2-benzisothiazolin-3-one and use of such combinations in controlling fungal and/or bacterial growth in aqueous systems, particularly in metalworking fluids, such as soluble-oil, semi-synthetic and synthetic metalworking fluids.

2. Description of Related Art

Iodopropargyl compounds, i.e. compounds containing a propargyl group and an iodine on the acetylenic carbon, are known to be useful in controlling bacteria and fungi in various aqueous systems. U.S. Pat. Nos. 4,259,350; 4,719,227; 4,616,004; 3,923,870; and 4,592,773, incorporated herein by reference, set forth various examples of iodopropargyl compounds with microbicidal properties.

One such iodopropargyl compound is iodopropargyl carbamate. The preparation and use of iodopropargyl carbamate as a microbicide and a preservative is described in U.S. Pat. No. 4,945,109; the disclosure of which is incorporated herein by reference.

Another such iodopropargyl compound is 3-iodopropargyl-N-butylcarbamate (IPBC). This compound is manufactured and sold by Troy Chemical Company under various names such as Polyphase® product, Polyphase® AF-1 product, and Polyphase® NP-1 product.

Although good microbicides, iodopropargyl compounds are expensive. Systems requiring high concentrations of iodopropargyl compounds are generally uneconomical.

The compound 1,2-benzisothiazolin-3-one has been used to control microbial growth for a long time. This compound is sold as Proxel® CRL product, or Proxel® GXL product.

As can be seen in Examples 1, 2 and 3, Table 1 (see Samples 8-10), and Tables 2 and 3 (Samples 15-18), high concentrations of 1,2-benzisothiazolin-3-one are required to control both bacterial and fungal growth in metalworking fluids.

Both of these types of products are used alone to control microorganisms in industrial fluids, since many industries, such as the machining industry, experience problems caused by microorganisms. Aqueous metalworking fluids or cutting fluids used in the machining industry are particularly susceptible to fouling caused by microorganisms. In machining operations, metalworking fluids are used primarily to reduce friction and heat, thereby reducing wear and prolonging the life of equipment.

Unfortunately, metalworking fluids have properties which are ideal for the growth of bacteria and fungi. Although bacteria are important in the biodeterioration of metalworking fluids, fungi and yeast play an important role as well. (Bennett, E.O., "The Deterioration of Metalworking Fluids", *Prog. Industrial Microbiology*, 13:121 (1974)).

Frequently, these microorganisms can cause the buildup of microbial deposits on machine surfaces, the clogging of jets and lines, the deterioration of the properties of the metalworking fluid itself, enhanced corrosion, and health and odor problems. When affected or deteriorated by the growth of microorganisms, the metalworking fluid loses many of its essential properties. The pH of the fluid may drop and other chemical changes may occur until the fluid can no longer provide adequate lubrication. At this point, the fluid must be replaced with fresh fluid, which is costly and results in loss of production time.

As a result of these problems, biocides are used extensively in metalworking fluid systems. Biocides may be incorporated in fluid concentrate or added to diluted fluids once they are in the holding tanks of the machine works.

There are many commercially available biocides. Some are of questionable utility because they have undesirable odors, or create hazards with respect to storage, use or handling. Consequently, workers in the trade have continued to seek improved biocides.

Economic factors, particularly the cost of the biocide and the expense of its application, can also be important factors when choosing a particular biocide for use in metalworking fluid systems. The cost performance index of any biocide is derived from the basic cost of the material, its effectiveness per unit weight, the duration of its biocidal or biostatic effect in the system treated, and the ease and frequency of its addition to the system treated.

Workers in the trade continue to seek a commercially available biocide capable of exhibiting a prolonged biocidal effect at normal use levels. Physical conditions, such as temperature and chemical reactivity with ingredients present in the system, often diminish or eliminate the effectiveness of prior art biocides known to the inventors. For example, many systems contain organic material which may react with a specific biocide and render the biocide ineffective.

Metalworking fluid systems in which heavy microbial growth occurs can especially benefit from the practice of the present invention. The practice of the present invention can also benefit many other aqueous systems, whether or not heavy microbial growth occurs, because of the reduction in frequency and quantity of the use of biocides.

SUMMARY OF THE INVENTION

An object of the present invention is to control fungal or bacterial growth in an aqueous system, such as a metalworking or cutting fluid, through the use of a synergistic combination of an iodopropargyl compound and benzisothiazolone.

Additional objects and advantages of the invention will be set forth in part in the description which follows, and in part will be obvious from the description, or may be learned by practice of the present invention. The objects and advantages of the invention will be realized and attained by means of the elements and combinations particularly pointed out in the appended claims.

To achieve the objects and in accordance with the purpose of the present invention, as embodied and broadly described herein, the present invention is a composition comprising (a) an iodopropargyl compound and (b) 1,2-benzisothiazolin-3-one, the composition containing an amount of (a) and (b) synergistically effective to reduce the growth of at least one microorganism.

A further embodiment is a metalworking fluid comprising (a) an iodopropargyl compound and (b) 1,2-benzisothiazolin-3-one, the fluid containing an amount of (a) and (b) synergistically effective to reduce the growth of at least one microorganism in said fluid.

A third embodiment is a concentrated metalworking fluid comprising (a) an iodopropargyl compound and (b) 1,2-benzisothiazolin-3-one, the concentrated fluid containing an amount of (a) and (b) synergistically effective to reduce the growth of at least one microorganism in the fluid when diluted and used at a metalworking site.

An additional embodiment according to the present invention is a method of controlling the growth of at least one microorganism in an aqueous fluid comprising the step of adding to the fluid a composition comprising (a) an iodopropargyl compound and (b) 1,2-benzisothiazolin-3-one, in a synergistically effective amount to control said growth.

Another embodiment is a method of controlling the growth of at least one microorganism in a diluted metalworking fluid comprising the step of separately adding to said diluted metalworking fluid: (a) an iodopropargyl compound and (b) 1,2-benzisothiazolin-3-one, where the ratio of (a) to (b) after addition of both components is from about 1:99 to 99:1. The combined amount of separately added (a) and (b) is synergistically effective to control the growth of the microorganism in the fluid.

A further embodiment is a method of controlling the growth of at least one microorganism in a diluted metalworking fluid comprising the step of adding to a diluted metalworking fluid: (a) an iodopropargyl compound and (b) 1,2-benzisothiazolin-3-one, wherein the ratio of (a) to (b) after addition of both components is from about 1:99 to 99:1. The combined amount of added (a) and (b) is synergistically effective to control the growth of the microorganism in said fluid.

It is to be understood that both the foregoing general description and the following detailed description are exemplary and explanatory only and are not restrictive of the present invention, as claimed.

DETAILED DESCRIPTION OF THE INVENTION

The use of 1,2-benzisothiazolin-3-one and derivatives thereof to control microorganisms has been described in U.S. Pat. No. 3,517,022 and British Patents 848,130, 861,379, 884,542 and 976,028.

U.S. Pat. No. 4,830,657 describes synergistic antimicrobial compositions comprising 2-bromo-2-bromomethylglutaronitrile and 1,2-benzisothiazolin-3-one. Biocidal compositions comprising certain quarternary ammonium compounds and 1,2-benzisothiazolin-3-one have been described in U.S. Pat. No. 3,970,755.

British Patent No. 2,230,190 describes biocidal compositions comprising 1,2-benzisothiazolin-3-one and either an alkal metal salt of a 2-mercaptopyridine-1-oxide or a mixture of 2,2'-dithiopyridine-1,1'-dioxide together with a salt of a metal. The patent also discloses that other known anti-microbial compounds can be added to this composition including among others, p-chlorophenyl-3-iodoproparyl formaldehyde. British Patent No. 2,208,474 describes biocodal compositions involving an isothiazolinone or an isothiazolinone derivative such as 1,2-benzisothiazolin-3-one and certain disulfide compounds.

Japanese Patent No. 6071-009 describes antimicrobial composition containing 2-(thiocyanomethylthio)benzothiazole and 1,2-benzisothiazolin-3-one. Japanese Patent No. 2087-230 describes antimicrobial composition comprising alkylpoly(aminoethyl)glycine salt and 1,2-benzisthiazolin-3-one.

The compound, 1,2-benzisothiazolin-3-one, is presently sold as a solid or in varying concentrations in suitable solvents such as dipropylene glycol under such commercial names as Proxel ® CRL product and Proxel ® GXL product.

An iodopropargyl compound for use in the present invention can be identified by the structure shown below:

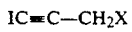

$$IC\equiv C-CH_2X$$

wherein X can be (1) oxygen which is part of an organic functional group; (2) nitrogen which is an organic functional group; (3) sulfur which is part of an organic functional group; or (4) carbon which is part of an organic functional group.

The functional group of which oxygen is a part is preferably an ether, ester or carbamate group. The functional group of which nitrogen is a part is preferably an amine, amide or carbamate group. The functional group of which sulfur is a part is preferably a thiol, thiane, sulfone or sulfoxide group. The organic functional group of which carbon is a part is preferably an ester, carbamate or alkyl group.

The iodopropargyl compounds set forth in U.S. Pat. Nos. 4,259,350, 4,719,227, 4,616,004, 3,923,870, 4,592,773 and 4,945,109 can be used for purposes of the present invention. The disclosures of these patents are specifically incorporated by reference herein.

The iodopropargyl compound may be chosen from a wide variety of known chemicals based on the compatibility of these compounds with metalworking fluids or other aqueous systems in use. Compatibility is determined by criteria such as solubility in the fluid system and lack of reactivity with the fluid or other components in the fluid, i.e. formation of precipitates of the iodopropargyl compounds reduces the effectiveness of the microbicide.

The compatibility is readily determined by one of ordinary skill by adding the iodopropargyl compound to the fluid to be used. It is preferred that the iodopropargyl compound be freely soluble in the particular fluid resulting in a uniform solution.

Iodopropargyl compounds, e.g., iodopropargyl carbamate and 3-iodopropargyl-N-butyl carbamate, are known to be compatible with soluble oil, semi-synthetic and synthetic metalworking fluids. One iodopropargyl carbamate formulation is known as BL-1120, a product manufactured by Buckman Laboratories as a 20% emulsifiable concentrate.

In the following discussion of preferred embodiments, component (a) is the BL-1120 product which contains 20% of the active ingredient iodopropargyl carbamate. Component (b) is the Proxel ® GXL product, supplied as a 17% solution of the active ingredient 1,2-benzisothiazolin-3-one.

As described above, components (a) and (b) are used in synergistically effective amounts. The ratio of component (a) to component (b) preferably ranges from 1:99 to 99:1, more preferably from 20:80 to 80:20, and most preferably 80:20. Another ratio of component (a) to (b) is from 40:60 to 60:40.

When two chemical microbicides are combined into one product or added separately three results are possible:
1) The resulting product would produce an additive (neutral) effect.
2) The chemicals in the product would produce an antagonistic effect, or
3) The chemicals in the product would produce a synergistic effect.

An additive effect has no economic advantage over the individual components. The antagonistic effect would produce a negative impact. Only synergism, which is less likely than either an additive or antagonistic effect, would produce a positive effect and therefore would be of economic advantage.

It is well-known in the microbicidal literature that there is no theoretical method to provide a reasonable likelihood of knowing, before actually testing, whether additive, antagonistic or synergistic effects will be obtained when two biocides are mixed to yield a new formulation.

The benefits of the present invention are most evident in systems that are highly contaminated with microorganisms. These are systems with bacterial and fungal counts greater than about $1.0 \times 10^6$/mL which are incapable of experiencing substantial count reduction when treated separately with low dosages of either an iodopropargyl compound or 1,2-benzisothiazolin-3-one.

For instance, compositions of the present invention can effectively be included, for example, in metalworking fluids, and concentrated metalworking fluids, and the compositions of the present invention can be used in methods for controlling the growth of microorganisms in an aqueous fluid, controlling the growth of microorganisms in a diluted metalworking fluid, and reducing the growth of microorganisms in a diluted metalworking fluid. These methods will be apparent based on the working examples that follow.

In these systems, a low concentration of 1,2-benzisothiazolin-3-one biocide or an iodopropargyl compound fails to provide adequate preservation. Evidence of adequate preservation or control is shown by a reduction to and maintenance of a bacterial count of less than about $1 \times 10^5$ per mL and fungal count of less than about $1 \times 10^3$ per mL for a period of not less than about six weeks.

One of the unique features of the present invention is that when 1,2-benzisothiazolin-3-one is used in conjunction with an iodopropargyl compound, it is possible in many instances, at certain concentrations and ratios of components, to achieve excellent fluid preservation, i.e. reducing the total fungal or bacterial count to undetectable limits and maintaining it at that level for a significant period. When either of the biocides is used alone in the concentration that was effective when used in the synergistic combination, each fails to achieve and maintain such a low level of microbial growth.

The synergistic activity of the combinations described above has been confirmed using standard laboratory techniques as illustrated below. The following examples are intended to illustrate, not limit, the present invention.

The test method employed was the Standard Method for the Evaluation of Antimicrobial Agents in Aqueous Metalworking Fluids (ASTM Designation: E686-80).

The ASTM test is a multiple challenge test designed to simulate industrial conditions. A formulation of the biocides is added separately to 600 mL aliquots of a metalworking fluid dilution. Controls contained only one of the biocides or no biocide.

The metalworking fluid samples are then inoculated with 1 ml of a mixed, partially defined microbial culture to give an initial bacterial count of approximately $1 \times 10^6$ and fungal count of not less than about $1 \times 10^3$ and aerated continuously. The system is aerated to provide oxygen for the growth of the microorganisms and also to simulate the industrial rolling of the coolant.

Every week, for a minimum of 6 weeks or until the test fails, the metalworking fluid samples are measured for microbial growth. This is done by enumerating the bacteria and fungi using standard plate-counting techniques.

The microorganisms used in the metalworking fluid inoculum included:
1) Fusarium sp. and bacteria obtained from a spoiled industrial fluid.
2) *Staphylococcus aureus*
3) *Pseudomonas aeruginosa*
4) *Klebsiella pneumoniae*
5) *Escherichia coli*

After six weeks, a bacterial count of less than about $1 \times 10^5$ per mL and a fungal count of less than about $1 \times 10^3$ per mL was indicative of adequate preservation.

In general, however, an effective fungicidal and bactericidal response can be obtained when the synergistic combination is employed in concentrations ranging from about 0.1 to about 5000 ppm of 1,2-benzisothiazolin-3-one, preferably 0.1 to 1000 ppm, and from about 0.1 to about 5000 ppm of an iodopropargyl carbamate, preferably 0.1 to 500 ppm.

EXAMPLE 1

Synergistic combinations of an iodopropargyl carbamate and 1,2-benzisothiazolin-3-one for use in soluble oil metalworking fluids.

Component (a) is a 20% solution of iodopropargyl carbamate, BL-1120 product, and component (b) is a 17% solution of 1,2-benzisothiazolin-3-one. Components (a) and (b) are added in different weight ratios and amounts to the diluted metalworking fluids and tested according to the test methods described previously.

The ppm amounts for components (a) and (b) in this Example and subsequent Examples refer to the amounts of each respective component in the fluids tested.

The results are set forth in Table 1. As can be seen in Table 1, when used alone, neither 250 ppm of component (a) (Sample 6) nor 100 ppm of component (b) (by extrapolation) was effective in preserving the soluble oil metalworking fluid and they all failed in the first two weeks. In contrast, when used in combination there was significant potentiation in antimicrobial activity lasting for over six weeks (Sample 3). Similarly, Sample 2 shows a synergistic effect in the effective control of bacterial and fungal growth.

TABLE 1

Preservation properties of combinations of (a) iodopropargyl carbamate and (b) 1,2-benzisothiazolin-3-one in a soluble metalworking fluid.

| Sample | BL-1120 (a) | Proxel GXL (b) | | 1 | 2 | 3 | 4 | 5 | 6 |
|---|---|---|---|---|---|---|---|---|---|
| 1 | | | B | — | $3.3 \times 10^7$ | $6 \times 10^7$ | $4.3 \times 10^7$ | $6 \times 10^7$ | $4.5 \times 10^7$ |
| 1 | 0 | 0 | F | ND — | $10^3$ | $10^2$ | $10^3$ | $10^3$ | $10^3$ |
| 2 | 250 | 250 | B | — | $<10$ | $<10$ | 30 | $<10$ | $1.8 \times 10^3$ |
| 2 | | | F | — | $<10$ | $<10$ | $<10$ | $<10$ | $<10$ |
| 3 | 250 | 100 | B | — | 20 | $<10$ | $<10$ | 20 | $1.4 \times 10^3$ |
| 3 | | | F | — | $<10$ | $<10$ | $<10$ | $<10$ | $<10$ |
| 4 | 250 | 50 | B | — | 20 | $<10$ | $8.6 \times 10^4$ | $7 \times 10^4$ | $1.4 \times 10^5$ |
| 4 | | | F | — | $<10$ | $<10$ | $<10$ | $<10$ | $<10$ |
| 5 | 100 | — | B | — | $1.9 \times 10^7$ | $3.5 \times 10^7$ | $1.6 \times 10^7$ | $9 \times 10^6$ | $1.0 \times 10^7$ |
| 5 | | | F | — | $<10$ | $<10$ | $<10$ | $<10$ | $<10$ |
| 6 | 250 | — | B | — | $5.1 \times 10^6$ | $1.8 \times 10^7$ | $1.7 \times 10^7$ | $1.3 \times 10^7$ | $1.1 \times 10^7$ |
| 6 | | | F | — | $<10$ | $<10$ | $<10$ | $<10$ | $<10$ |
| 7 | 500 | — | B | — | $<10$ | $<10$ | 30 | $<10$ | $2.9 \times 10^3$ |
| 7 | | | F | — | $<10$ | $<10$ | $<10$ | $<10$ | $<10$ |
| 8 | — | 250 | B | — | $1.0 \times 10^5$ | $9 \times 10^5$ | $1.3 \times 10^6$ | $1.3 \times 10^6$ | $1.2 \times 10^6$ |
| 8 | | | F | — | $<10$ | $<10$ | $<10$ | $<10$ | $<10$ |
| 9 | — | 500 | B | — | $3.6 \times 10^5$ | $6.6 \times 10^5$ | $3.2 \times 10^5$ | $4.7 \times 10^5$ | $4.3 \times 10^5$ |
| 9 | | | F | — | $<10$ | $<10$ | $<10$ | $<10$ | $<10$ |
| 10 | — | 1000 | B | — | 20 | $2.0 \times 10^5$ | $5.7 \times 10^5$ | $3 \times 10^5$ | $1.8 \times 10^5$ |
| 10 | | | F | — | $<10$ | $<10$ | $<10$ | $<10$ | $<10$ |

ND = Not determined
B = Bacterial count (cfu/mL)
F = Fungal count (cfu/mL)

EXAMPLE 2

Synergistic combinations for an iodopropargyl carbamate and 1,2-benzisothiazolin-3-one for use in synthetic metalworking fluids.

Component (a) is a 20% solution of iodopropargyl carbamate, BL-1120 product, and component (b) is a 17% solution of 1,2-benzisothiazolin-3-one. Components (a) and (b) are added in different weight ratios and amounts to the diluted metalworking fluids and tested according to the test methods described previously.

The results are set forth in Table 2. As can be seen in Table 2, when used alone 25 ppm of component (a) (Sample 11) preserved the synthetic metalworking fluid for only one week and 250 ppm of component (b) (Sample 16) failed in the first week. In contrast, when used in combination, (Sample 9) they effectively preserved the metalworking fluid for six weeks. Similarly, Samples 2-8 show a synergistic result in the effective control of bacterial and fungal growth in the metalworking fluid.

TABLE 2

Preservation properties of combinations of (a) iodopropargyl carbamate and (b) 1,2-benzisothiazolin-3-one in a synthetic metalworking fluid.

| Sample | BL-1120 (a) | Proxel GXL (b) | | 1 | 2 | 3 | 4 | 5 | 6 |
|---|---|---|---|---|---|---|---|---|---|
| 1 | 0 | 0 | B | $3.0 \times 10^7$ | $9.8 \times 10^8$ | $2.5 \times 10^9$ | $3.3 \times 10^{10}$ | $3.6 \times 10^7$ | $1.8 \times 10^7$ |
| 1 | | | F | $10^5$ | $3 \times 10^5$ | $10^5$ | $6 \times 10^6$ | $10^5$ | $10^5$ |
| 2 | 100 | 500 | B | $7 \times 10^2$ | $7 \times 10^3$ | $4.9 \times 10^3$ | $10^3$ | $4.2 \times 10^3$ | $1.2 \times 10^2$ |
| 2 | | | F | $<10$ | $<10$ | $<10$ | $<10$ | $<10$ | $<10$ |
| 3 | 100 | 250 | B | $<10$ | 20 | $4.3 \times 10^2$ | $9.4 \times 10^2$ | $4.1 \times 10^3$ | $1.9 \times 10^4$ |
| 3 | | | F | $<10$ | $<10$ | $<10$ | $<10$ | $<10$ | $<10$ |
| 4 | 100 | 100 | B | $<10$ | 60 | $5.3 \times 10^2$ | $1.3 \times 10^3$ | $1.4 \times 10^4$ | $2.2 \times 10^4$ |
| 4 | | | F | $<10$ | $<10$ | $<10$ | $<10$ | $<10$ | $<10$ |
| 5 | 50 | 500 | B | $4 \times 10^2$ | $4.2 \times 10^3$ | $8.6 \times 10^3$ | $10^3$ | $1.0 \times 10^3$ | $2 \times 10^3$ |
| 5 | | | F | $<10$ | $<10$ | $<10$ | $<10$ | $<10$ | $<10$ |
| 6 | 50 | 250 | B | $<10$ | 20 | $8.7 \times 10^2$ | $2 \times 10^3$ | $7.3 \times 10^3$ | $1.3 \times 10^4$ |
| 6 | | | F | $<10$ | $<10$ | $<10$ | $<10$ | $<10$ | $<10$ |
| 7 | 50 | 100 | B | 30 | $3.1 \times 10^2$ | $7.5 \times 10^2$ | $8 \times 10^2$ | $9 \times 10^3$ | $3 \times 10^4$ |
| 7 | | | F | $<10$ | $<10$ | $<10$ | $<10$ | $<10$ | $<10$ |
| 8 | 25 | 500 | B | $5.6 \times 10^2$ | $4.8 \times 10^3$ | $2.5 \times 10^3$ | $10^3$ | $7.1 \times 10^3$ | $3.1 \times 10^3$ |
| 8 | | | F | $<10$ | $<10$ | $<10$ | $<10$ | $<10$ | $<10$ |
| 9 | 25 | 250 | B | $<10$ | 40 | $9.8 \times 10^2$ | $8.5 \times 10^2$ | $6.2 \times 10^3$ | $2.2 \times 10^4$ |
| 9 | | | F | $<10$ | $<10$ | $<10$ | $<10$ | 20 | $<10$ |
| 10 | 25 | 100 | B | $7.2 \times 10^3$ | $1.4 \times 10^5$ | $9.3 \times 10^4$ | $1.6 \times 10^4$ | $1.9 \times 10^5$ | $10^6$ |
| 10 | | | F | $<10$ | $<10$ | $<10$ | $<10$ | $<10$ | $<10$ |
| 11 | 25 | — | B | $6.4 \times 10^4$ | $7.4 \times 10^5$ | $1.3 \times 10^6$ | $3.2 \times 10^6$ | $6.1 \times 10^6$ | $1.3 \times 10^7$ |
| 11 | | | F | $<10$ | $<10$ | $<10$ | $<10$ | $<10$ | $<20$ |
| 12 | 50 | — | B | $7.6 \times 10^2$ | $2.3 \times 10^4$ | $4.6 \times 10^5$ | $7.6 \times 10^6$ | $3.9 \times 10^7$ | $4.9 \times 10^7$ |
| 12 | | | F | $<10$ | $<10$ | $<10$ | $<10$ | $<10$ | $<10$ |
| 13 | 100 | — | B | $<10$ | 50 | $6.2 \times 10^2$ | $2.6 \times 10^3$ | $2.4 \times 10^6$ | $2.5 \times 10^7$ |
| 13 | | | F | $<10$ | $<10$ | $<10$ | $<10$ | $<10$ | $<10$ |
| 14 | 250 | — | B | $<10$ | $<10$ | $<10$ | $<10$ | $<10$ | $<10$ |
| 14 | | | F | $<10$ | $<10$ | $<10$ | $<10$ | $<10$ | $<10$ |

TABLE 2-continued

Preservation properties of combinations of (a) iodopropargyl carbamate and
(b) 1,2-benzisothiazolin-3-one in a synthetic metalworking fluid.

| Sample | Biocide Levels (ppm) BL-1120 (a) | Proxel GXL (b) | | Microbial counts at indicated exposure times (weeks) | | | | | |
|---|---|---|---|---|---|---|---|---|---|
| | | | | 1 | 2 | 3 | 4 | 5 | 6 |
| 15 | — | 100 | B | $7.6 \times 10^6$ | $1.1 \times 10^7$ | $1.7 \times 10^8$ | $7.6 \times 10^7$ | $10^9$ | $1.4 \times 10^8$ |
| 15 | | | F | $2.0 \times 10^5$ | $2.9 \times 10^5$ | $1.6 \times 10^6$ | $2.5 \times 10^5$ | $4.5 \times 10^6$ | $4 \times 10^5$ |
| 16 | — | 250 | B | $3.6 \times 10^5$ | $4.5 \times 10^6$ | $1.1 \times 10^7$ | $1.1 \times 10^7$ | $8.6 \times 10^7$ | $10^8$ |
| 16 | | | F | $9.1 \times 10^5$ | $3.3 \times 10^5$ | $6.1 \times 10^5$ | $2.4 \times 10^5$ | $2.9 \times 10^5$ | $5.2 \times 10^5$ |
| 17 | — | 500 | B | 50 | 60 | $6.5 \times 10^2$ | $1.7 \times 10^4$ | $3.5 \times 10^6$ | $4.2 \times 10^6$ |
| 17 | | | F | $7.3 \times 10^2$ | $1.4 \times 10^4$ | $5.1 \times 10^4$ | $2.5 \times 10^4$ | $10^4$ | $10^5$ |
| 18 | — | 1000 | B | $3.0 \times 10^2$ | $8.8 \times 10^3$ | $2.5 \times 10^3$ | $3 \times 10^3$ | $7.1 \times 10^2$ | $6.1 \times 10^2$ |
| 18 | | | F | <10 | <10 | <10 | <10 | <10 | <10 |

B = Bacterial count (cfu/mL)
F = Fungal count (cfu/mL)

EXAMPLE 3

Synergistic combinations of an iodopropargyl carbamate and 1,2-benzisothiazolin-3-one for use in semi-synthetic metalworking fluids.

Component (a) is a 20% solution of iodopropargyl carbamate, BL-1120 product, and component (b) is a 17% solution of 1,2-benzisothiazolin-3-one, Proxel GXL product. Components (a) and (b) are added in different weight ratios and amounts to the diluted metalworking fluids and tested according to the test methods described previously.

The results are set forth in Table 3. As can be seen in Table 3, when used alone, 50 ppm of component (a) (Sample 12) preserved the semi-cynthetic metalworking fluid for only two weeks and 100 ppm of component (b) (Sample 15) was completely ineffective and failed in the first week. In contrast, when used in combination (Sample 7) they effectively preserved the metalworking fluid for six weeks. Similarly, Samples 5, 6 and 8 show a synergistic effect in the effective control of bacterial and fungal growth in the metalworking fluid.

TABLE 3

Preservation properties of (a) iodopropargyl carbamate and
(b) 1,2-benzisothiazolin-3-one in a semi-synthetic metalworking fluid.

| Sample | Biocide Levels (ppm) BL-1120 (a) | Proxel GXL (b) | | Microbial Contents at Indicated Exposure Times (weeks) | | | | | |
|---|---|---|---|---|---|---|---|---|---|
| | | | | 1 | 2 | 3 | 4 | 5 | 6 |
| 1 | 0 | 0 | B | $9.6 \times 10^7$ | $1.3 \times 10^8$ | $10^9$ | $7.5 \times 10^7$ | $7.3 \times 10^8$ | $1.4 \times 10^8$ |
| 1 | | | F | $1.6 \times 10^5$ | $2 \times 10^5$ | $2.1 \times 10^6$ | $4 \times 10^5$ | $6 \times 10^5$ | $10^5$ |
| 2 | 100 | 500 | B | 90 | $1.7 \times 10^2$ | $2.9 \times 10^3$ | $10^3$ | $1.1 \times 10^2$ | $6.8 \times 10^2$ |
| 2 | | | F | <10 | <10 | <10 | <10 | <10 | <10 |
| 3 | 100 | 250 | B | <10 | 90 | $1.9 \times 10^2$ | $8.7 \times 10^2$ | $5.7 \times 10^3$ | $1.1 \times 10^4$ |
| 3 | | | F | <10 | <10 | <10 | <10 | <10 | <10 |
| 4 | 100 | 100 | B | <10 | $1.5 \times 10^2$ | $5.8 \times 10^2$ | $1.2 \times 10^3$ | $7.7 \times 10^3$ | $8.9 \times 10^3$ |
| 4 | | | F | <10 | <10 | <10 | <10 | <10 | <10 |
| 5 | 50 | 500 | B | $2.9 \times 10^2$ | $5.5 \times 10^2$ | $6.2 \times 10^3$ | $10^3$ | $3 \times 10^2$ | $4.3 \times 10^3$ |
| 5 | | | F | <10 | <10 | <10 | <10 | <10 | <10 |
| 6 | 50 | 250 | B | 50 | 70 | $4.4 \times 10^2$ | $3.7 \times 10^2$ | $1.3 \times 10^4$ | $2.7 \times 10^4$ |
| 6 | | | F | <10 | <10 | <10 | <10 | <10 | <10 |
| 7 | 50 | 100 | B | 50 | 30 | $6.5 \times 10^2$ | $1.1 \times 10^3$ | $1.8 \times 10^4$ | $1.8 \times 10^4$ |
| 7 | | | F | <10 | <10 | <10 | <10 | <10 | <10 |
| 8 | 25 | 500 | B | $3.1 \times 10^2$ | $1.4 \times 10^3$ | $3 \times 10^3$ | $10^3$ | $1.3 \times 10^2$ | $2.2 \times 10^3$ |
| 8 | | | F | <10 | <10 | <10 | <10 | <10 | <10 |
| 9 | 25 | 250 | B | <10 | 90 | $7.0 \times 10^2$ | $6.4 \times 10^2$ | $1.1 \times 10^4$ | $2.3 \times 10^6$ |
| 9 | | | F | <10 | <10 | <10 | <10 | $10^2$ | $10^4$ |
| 10 | 25 | 100 | B | 60 | $1.1 \times 10^2$ | $8.7 \times 10^2$ | $4.1 \times 10^2$ | $10^6$ | $1.3 \times 10^8$ |
| 10 | | | F | <10 | <10 | <10 | $1.9 \times 10^2$ | $10^3$ | $10^5$ |
| 11 | 25 | — | B | $2.8 \times 10^3$ | $2.2 \times 10^4$ | $1.5 \times 10^6$ | $9.5 \times 10^6$ | $8.2 \times 10^7$ | $4.1 \times 10^7$ |
| 11 | | | F | <10 | <10 | <10 | <10 | $10^3$ | $1.9 \times 10^5$ | $1.3 \times 10^5$ |
| 12 | 50 | — | B | $2.3 \times 10^3$ | $7.2 \times 10^3$ | $1.0 \times 10^6$ | $2.3 \times 10^7$ | $1.1 \times 10^8$ | $7.2 \times 10^7$ |
| 12 | | | F | <10 | <10 | <10 | <10 | <10 | $10^3$ |
| 13 | 100 | — | B | 30 | $7.8 \times 10^2$ | $7.2 \times 10^2$ | $1.2 \times 10^3$ | $1.3 \times 10^4$ | $8.9 \times 10^3$ |
| 13 | | | F | <10 | <10 | <10 | <10 | <10 | <10 |
| 14 | 250 | — | B | <10 | <10 | <10 | <10 | <10 | <10 |
| 14 | | | F | <10 | <10 | <10 | <10 | <10 | <10 |
| 15 | — | 100 | B | $4.7 \times 10^7$ | $1.2 \times 10^8$ | $1.2 \times 10^7$ | $1.7 \times 10^7$ | $1.2 \times 10^8$ | $1.3 \times 10^8$ |
| 15 | | | F | $1.5 \times 10^5$ | $2 \times 10^5$ | $2.9 \times 10^5$ | $1.8 \times 10^5$ | $1.9 \times 10^5$ | $3.5 \times 10^5$ |
| 16 | — | 250 | B | $6 \times 10^2$ | $3.3 \times 10^6$ | $3.9 \times 10^6$ | $3.4 \times 10^6$ | $1.5 \times 10^7$ | $1.6 \times 10^7$ |
| 16 | | | F | $2.0 \times 10^5$ | $3.0 \times 10^5$ | $7.0 \times 10^5$ | $7 \times 10^5$ | $6 \times 10^5$ | $7 \times 10^5$ |
| 17 | — | 500 | B | 70 | 90 | $3.3 \times 10^6$ | $4.6 \times 10^6$ | $5.8 \times 10^6$ | $10^8$ |
| 17 | | | F | $10^2$ | $1.0 \times 10^4$ | $2.2 \times 10^4$ | $2.4 \times 10^4$ | $10^5$ | $10^5$ |
| 18 | — | 1000 | B | $2.5 \times 10^2$ | $4.2 \times 10^3$ | $3.4 \times 10^3$ | $3.1 \times 10^3$ | $1.4 \times 10^2$ | $2 \times 10^2$ |
| 18 | | | F | <10 | <10 | <10 | <10 | <10 | $2 \times 10^2$ |

B = Bacterial count (cfu/mL)
F = Fungal count (cfu/mL)

As seen from the above examples, the antifungal and antibacterial combinations described previously can have synergistic activity when employed at appropriate concentrations and may be used to inhibit the growth of fungi and bacteria in aqueous systems, such as metalworking fluids. It will be obvious to those skilled in the trade that the required synergistically effective amounts (concentrations) will vary depending on the particular organisms and particular applications, and can readily be determined by routine experimentation. Use of a synergistically effective amount enables the use of a substantially smaller amount of each of components (a) and (b) to achieve a given effect than would be necessary for each component if used alone, or than would be necessary if a mere additive effect from combining (a) and (b) were obtained.

What is claimed is:

1. A microbicidal composition comprising (a) iodopropargyl carbamate and (b) 1,2-benzisothiazolin-3-one, wherein said composition contains an amount of (a) and (b) synergistically effective to control or reduce the growth of at least one microorganism.

2. The composition of claim 1, wherein the microorganism is selected from the group consisting of bacteria and fungi.

3. The composition of claim 1, wherein the ratio of (a) and (b) is from 1:99 to 99:1.

4. The composition of claim 3, wherein said ratio is from 20:80 to 80:20.

5. The composition of claim 4, wherein said ratio is 40:60 to 60:40.

6. The composition of claim 1, wherein the concentration of (a) ranges from 0.1 ppm to 5000 ppm and the concentration of (b) ranges from 0.1 ppm to 5000 ppm.

7. The composition of claim 1, wherein the concentration of (a) ranges from 0.1 ppm to 1000 ppm and the concentration of (b) ranges from 0.1 ppm to 500 ppm.

8. A method of controlling or reducing the growth of at least one microorganism in an aqueous fluid comprising the step of adding to said fluid a microbicidal composition comprising (a) iodopropargyl carbamate and (b) 1,2-benzisothiazolin-3-one in a synergistically effective amount to control or reduce said growth.

9. The method of claim 8, wherein said microorganism is selected from the group consisting of bacteria and fungi.

10. The method of claim 8, wherein said aqueous fluid is a metalworking fluid.

11. The method of claim 8, wherein said ratio is from 40:60 to 60:40.

12. The method of claim 8, wherein said aqueous fluid is a diluted metalworking fluid and the ratio of (a) and (b) after addition of both (a) and (b) to said fluid is from 1:99 to 99:1 and wherein the combined amount of separately added (a) and (b) is synergistically effective to control or reduce the growth of the microorganism in said fluid.

13. The method of claim 12, wherein said microorganism is selected from the group consisting of bacteria and fungi.

14. The method of claim 8, wherein said aqueous fluid is a diluted metalworking fluid and the ratio of (a) and (b) after addition of both (a) and (b) to said fluid is from 1:99 and 99:1 and wherein the combined amount of added (a) and (b) is synergistically effective to control or reduce the growth of the microorganism in said fluid.

15. The method of claim 14, wherein said ratio is from 20:80 to 80:20.

16. A metalworking fluid comprising a fluid and (a) iodopropargyl carbamate and (b) 1,2-benzisothiazolin-3-one; said fluid containing an amount of (a) and (b) synergistically effective to control or reduce the growth of at least one microorganism in said fluid.

17. The fluid of claim 16, wherein the ratio of (a) and (b) is from 1:99 to 99:1, and wherein said microorganism is selected from the group consisting of bacteria and fungi.

18. The metalworking fluid of claim 16, wherein said metalworking fluid is a concentrated metalworking fluid and (a) and (b) are present in an amount synergistically effective to control or reduce the growth of at least one microorganism in said fluid when said fluid is diluted and used at a metalworking site.

19. The composition of claim 18, wherein said microorganism is selected from the group consisting of bacteria and fungi.

* * * * *